United States Patent [19]

Nemirow

[11] Patent Number: 5,261,274
[45] Date of Patent: Nov. 16, 1993

[54] DYNAMIC VOLUMETRIC INSTRUMENT GAUGE

[75] Inventor: Daniel M. Nemirow, 6812 157th Pl. SW., Edmonds, Wash. 98020

[73] Assignee: Daniel M. Nemirow, Edmonds, Wash.

[21] Appl. No.: 528,921

[22] Filed: May 25, 1990

[51] Int. Cl.$^5$ ............................................ G01F 23/22
[52] U.S. Cl. .................................. 73/149; 73/290 V; 324/668; 364/509; 367/908
[58] Field of Search .................. 73/149, 290 V, 290 R, 73/597, 659, 579, 581, 592, 580; 364/178, 179, 562, 571, 509; 340/618, 621; 367/908, 902; 324/633, 634, 635

[56] References Cited

U.S. PATENT DOCUMENTS

| | | | |
|---|---|---|---|
| 2,990,543 | 6/1961 | Rod | 73/290 V X |
| 3,596,510 | 8/1971 | Paine | 73/149 |
| 3,757,285 | 9/1973 | Ferré | 367/902 |
| 3,962,919 | 6/1976 | Playfoot et al. | 73/290 V |
| 4,016,746 | 4/1977 | Paredes-Galvan | 73/580 X |
| 4,074,244 | 2/1978 | Balderson | 340/618 |
| 4,167,874 | 9/1979 | Grant | 73/290 R |
| 4,300,131 | 11/1981 | Mitsui et al. | 340/618 |
| 4,370,888 | 2/1983 | Popper | 73/580 |
| 4,400,976 | 8/1983 | Blades | 73/290 V |
| 4,474,061 | 10/1984 | Parker | 73/290 V |
| 4,535,627 | 8/1985 | Prost et al. | 73/149 |
| 4,599,892 | 7/1986 | Doshi | 73/149 |
| 4,675,854 | 6/1987 | Lau | 73/290 V |
| 4,685,326 | 8/1987 | Peterson | 73/580 |
| 4,704,902 | 11/1987 | Doshi | 73/290 V |
| 4,777,821 | 10/1988 | Gerve | 73/290 V |
| 4,811,595 | 3/1989 | Marciniak et al. | 73/290 V |
| 4,901,245 | 2/1990 | Olson et al. | 367/908 |
| 4,908,783 | 3/1990 | Maier | 340/618 |
| 4,930,511 | 6/1990 | Rossman et al. | 73/597 |
| 4,954,997 | 9/1990 | Dieulesaint et al. | 367/908 |
| 5,054,318 | 10/1991 | Lew | 73/290 V |
| 5,076,100 | 12/1991 | Hunter et al. | 73/290 V |

FOREIGN PATENT DOCUMENTS 2199948 7/1988 United Kingdom ............. 73/290 V

Primary Examiner—Daniel M. Yasich

[57] ABSTRACT

This instrument contains a transducer and a sensor that are mounted on the exterior surface of a liquid container or tank. The transducer is tuned by electronic signals to the mechanical resonant frequency of the liquid container or tank. The sensor converts the mechanical vibrations into dynamic electrical signals using electronic components. A phase detector and feedback circuitry force the transducer to track the resonant frequency of the tank as liquid is removed from the tank. The signal output of the feedback control circuitry is converted to display the amount of liquid remaining in the tank. The resonant frequency of the liquid container is a measure of the total mass of the container. This includes the tare weight of the container plus the weight of the liquid in the tank. The tare weight of the tank is a constant. The stiffness of the tank can be considered a constant. The dampening coefficient changes do not adversely effect the accuracy requirements of the instrument. Therefore, the change in resonant frequency of the tank as liquid is removed is nonlinear, but is an analytic function of the liquid remaining in the tank. Zero and span adjustments eliminate the effect of the constants and permit one design to satisfy many requirements. At resonance the amplitude response of the tank is much larger than the noise of the environment. As the intelligence of the instrument to interpret changes in liquid volume is a function of frequency, this adds to the noise immunity. The nonlinear dynamic response of the instrument is an asset in the use of this gauge for fuel tanks and other applications.

16 Claims, 7 Drawing Sheets

DYNAMIC VOLUMETRIC INSTRUMENT GAUGE

BACKGROUND

1. Field of the Invention

This invention relates to gauges for measuring liquid volume in liquid containers and tanks. More particularly, the invention relates to a dynamic gauge that uses signals that permit the installation of transducers or sensors on the outside surface of the containers.

2. Description of Prior Art

Other systems use capacitance probes, float actuated electro-mechanical devices, or differential pressure sensors immersed in the fluid. Ultrasonic transducer systems have been inserted in the top of the tank to measure liquid level. Similarly, acoustic systems have used transducers inserted in the tank to measure the volumetric change as fluid is removed from a tank. Strain gauges have been used on the exterior of the tank to measure the liquid weight or the volume of liquid remaining in the tank. Exterior mounting, or non-invasiveness, is obviously a desirable attribute, but strain gauges are expensive and have reliability problems even in environments that are only moderately hostile. All invasive systems, i.e. those that require the sensor or transducer to be inserted int he liquid container, have higher installation costs and usually are relatively unreliable, more expensive, and require more maintenance. These systems do not lend themselves to multi-tank applications easily.

SUMMARY OF THE INVENTION

This invention is the result of analysis to provide the best configuration for the liquid volumetric instrument gauges. For analysis and test three different liquids were considered. The liquids were gasoline, diesel fuel, and water. But, as the specified system depends on the change in weight of the tank as liquid is removed, other liquids could be substituted. Tests on prototype units, using dedicated interface hardware, software, and a personal computer proved earlier design analysis: that a single design approach would satisfy most requirements for a low cost and reliable liquid volumetric gauge.

Mounting the transducer and the sensor on the outside surface of the tank provided the improvement in reliability, maintainability, and cost of installation by at least one order of magnitude over the present electromechanical level gauges. Ease of installation and initial adjustment design also exceeds that of the present competitive gauges.

Several types of transducers were considered to excite the tank into mechanical resonance. Magnetostrictive, piezoelectric, sonarthumper, and moving coil transducers were analyzed for the major market requirements. All may be used for a variety of applications, but the magnetostrictive, piezoelectric, and moving coil transducers have been tested. The magnetostrictive devices will be described because of their high reliability under adverse environmental conditions.

An electrical signal applied to a wire coil wound around a magnetostrictive material will change the dimensions of the material at the same frequency as the applied signal. Mechanically coupled to a structure it can produce a vibration in the structure at the same frequency as the electrical signal. The frequency of the signal can then be varied until the structure of the liquid container resonates. Known components in the electronic circuitry can then interpret the resonance frequency in terms of the liquid volume remaining in the tank.

DRAWING FIGURES

FIG. 1. is a schematic diagram of a preferred embodiment of this invention;

FIG. 2. is a schematic diagram of a second embodiment of the invention to meet the requirements of acquiring volumetric data from a multi-tank system;

FIG. 3. is a schematic diagram of a third embodiment of the invention, showing a low cost volumetric gauge instrument;

Figure 5:
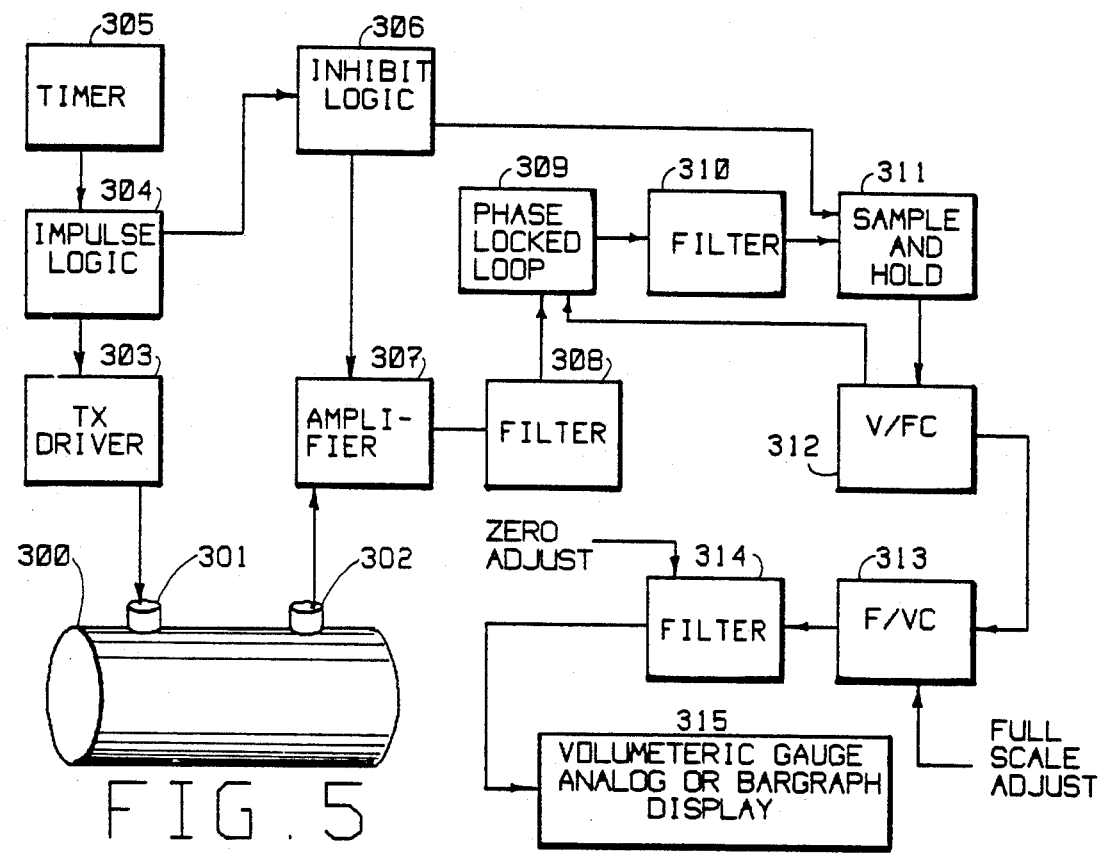
Figure 6:
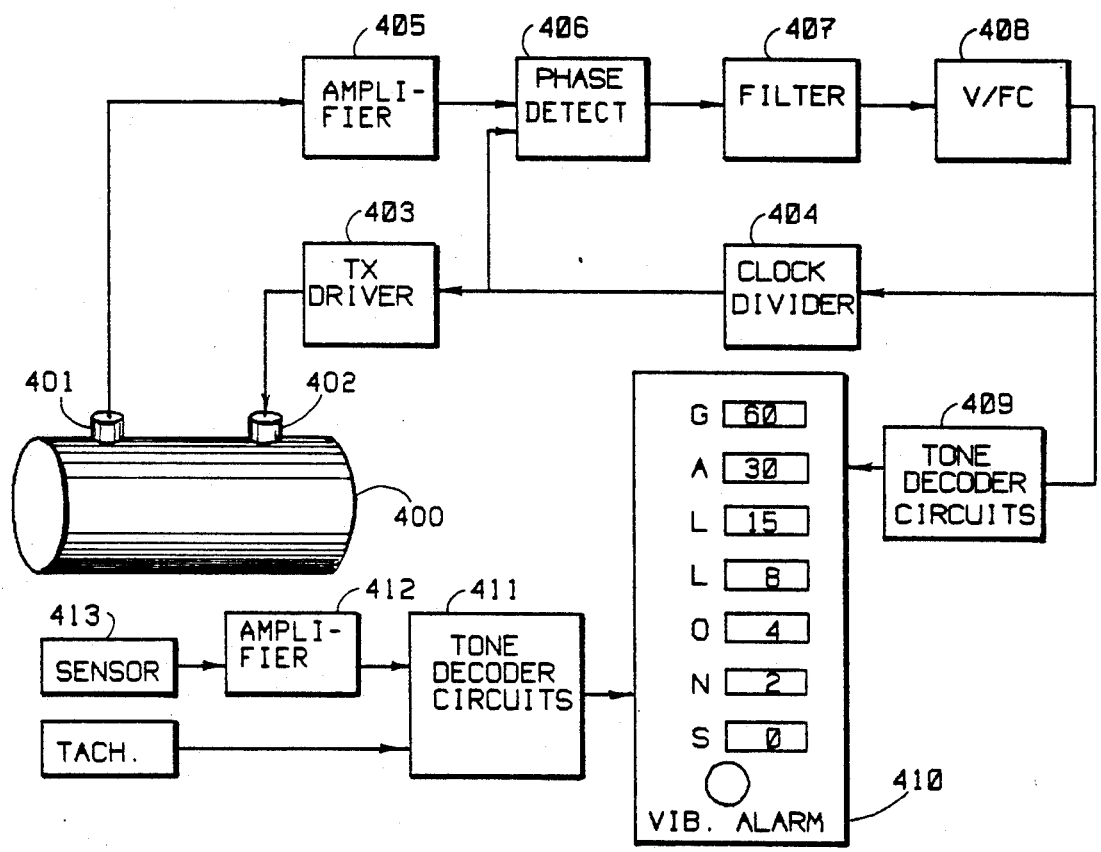
Figure 7:
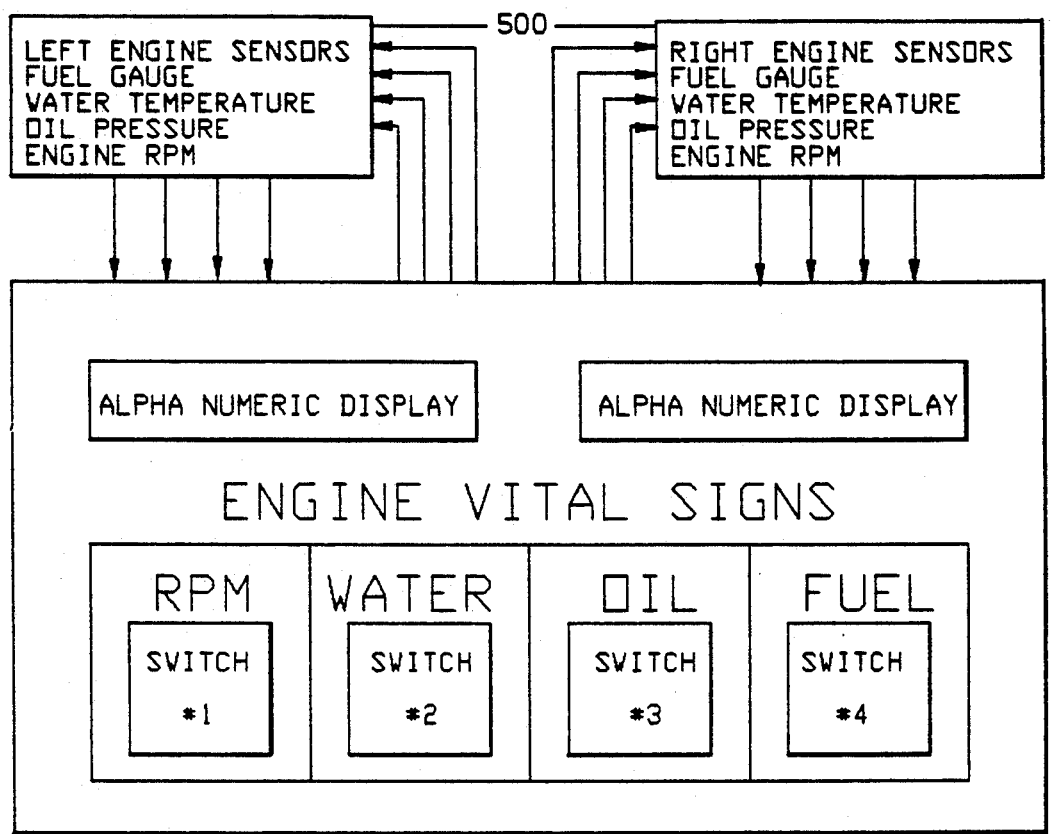

FIG. 5. is a schematic diagram of a fourth embodiment of the invention, showing a low cost volumetric gauge instrument;

FIG. 6. is a schematic diagram of a fifth embodiment of this invention meeting some of the requirements that are unique to the marine markets; and FIG. 7. is a schematic diagram of a sixth embodiment of the invention showing an arrangement for augmenting the usual instrumentation requirements of marine engines with a fuel gauge.

DETAILED DESCRIPTION OF THE PREFERRED EMBODIMENT

Figure 1:
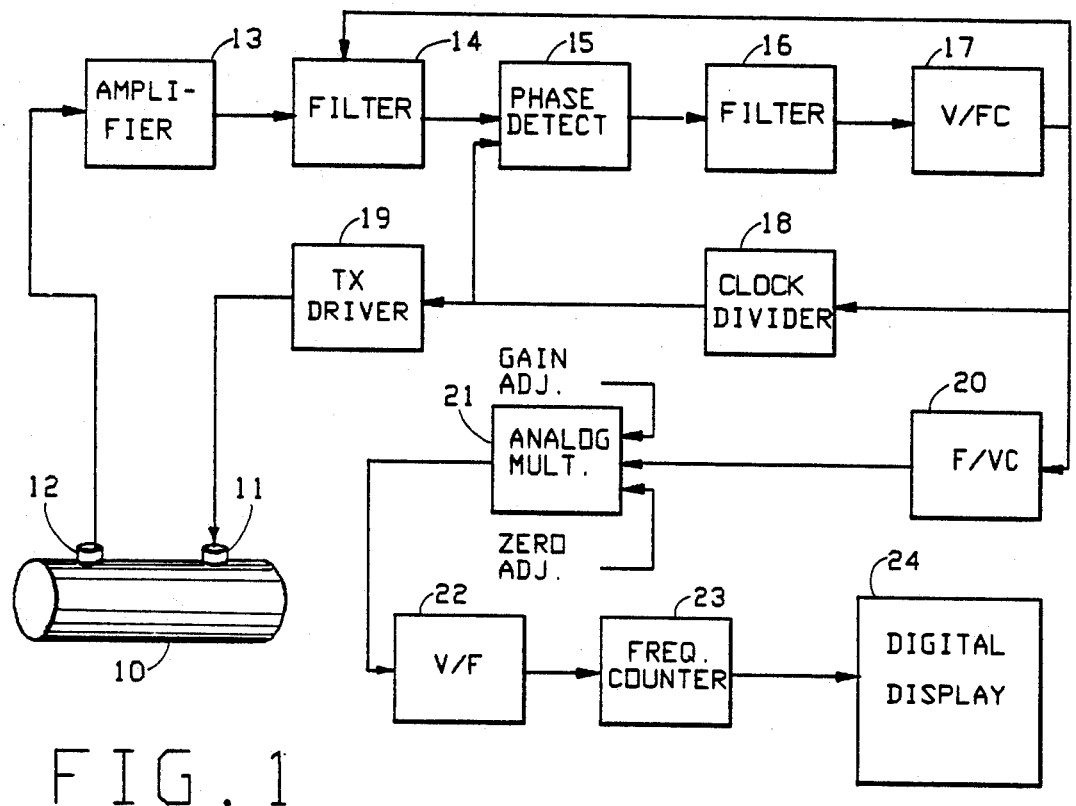

FIG. 1 describes a unique embodiment of this invention, wherein a transducer 11 and a sensor 12 are mounted on the exterior surface of a tank 10. The structural resonance of the tank is measured. The electronic circuitry provides the data manipulation to display on a volumetric display 24 the volume of fluid remaining in the tank 10.

This invention essentially consists of automatically tuning the tank 10 to its resonant frequency which is an analytic inverse exponential function of the volume of fluid remaining in the tank. Phase locked loop feedback control circuitry forces the transducer to change its frequency and track the resonant frequency received by the sensor.

This invention is also unique in that dynamic rather than static measurement techniques are used. Strain gauges are considered static devices. The transducers and sensors used in this invention are dynamic devices. Dynamic signals can be defined as those signals which vary as a function of time and the intelligence is in the frequency of the signal.

FIG. 1 displays the general design for a single tank system. The box elements in the circuits shown in the drawings are not shown in detail because they are all conventional off-the-shelf items known to those skilled in the art. The sensor 12 sends its dynamic signals to a suitable amplifier, which, in the case of a piezoelectric sensor would be a charge amplifier 13. The charge amplifier circuitry includes a bandpass filter and a line driver. The charge amplifier circuitry drives a switched capacitor filter 14. This filter 14 is controlled by the output of the voltage to frequency converter 17 and delivers its output to the phase detector 15. This phase detector drives a filter 16. The filter drives the voltage to frequency converter 17. The VFC 17, through a divide by 100 circuit 18 (better known as a "clock divider"), closes the loop to the phase detector 15 and drives a transducer driver 19 which drives the transducer to vibrate the tank at its resonance frequency. The VFC 17 drives conventional linearize circuits 20 which have a frequency-to-voltage converter driving an analog multiplier, the output of which is converted from an analog voltage signal back to a frequency signal in a voltage-to-frequency converter. These linearize circuits 20 convert the structural resonances to frequencies that can drive a volumetric display 24 through a counter 22. The flow display 23 is inoperative when the residual volume is greater than 20%. The flow display and the counter are both provided with clock information by the clock circuits 21.

The ZERO and SPAN (or GAIN) adjustments, which in practice would be made to the analog multiplier in the linearize circuits 20, permit a single system design to cover a wide range of applications. Similarly, the linearize circuits 20 will permit application to a wide range of liquid container configurations.

For many applications, the transducer TX 11 is a magnetostrictive component. This type of transducer changes its physical dimensions under the influence of a change in magnetic flux. Tests have shown that this type of a transducer provides an excellent method of transmitting vibrations into a mechanical structure. For some applications the sensor 12 is a piezoelectric film type component. This is a low cost, reliable, and easily installed component.

Figure 2:
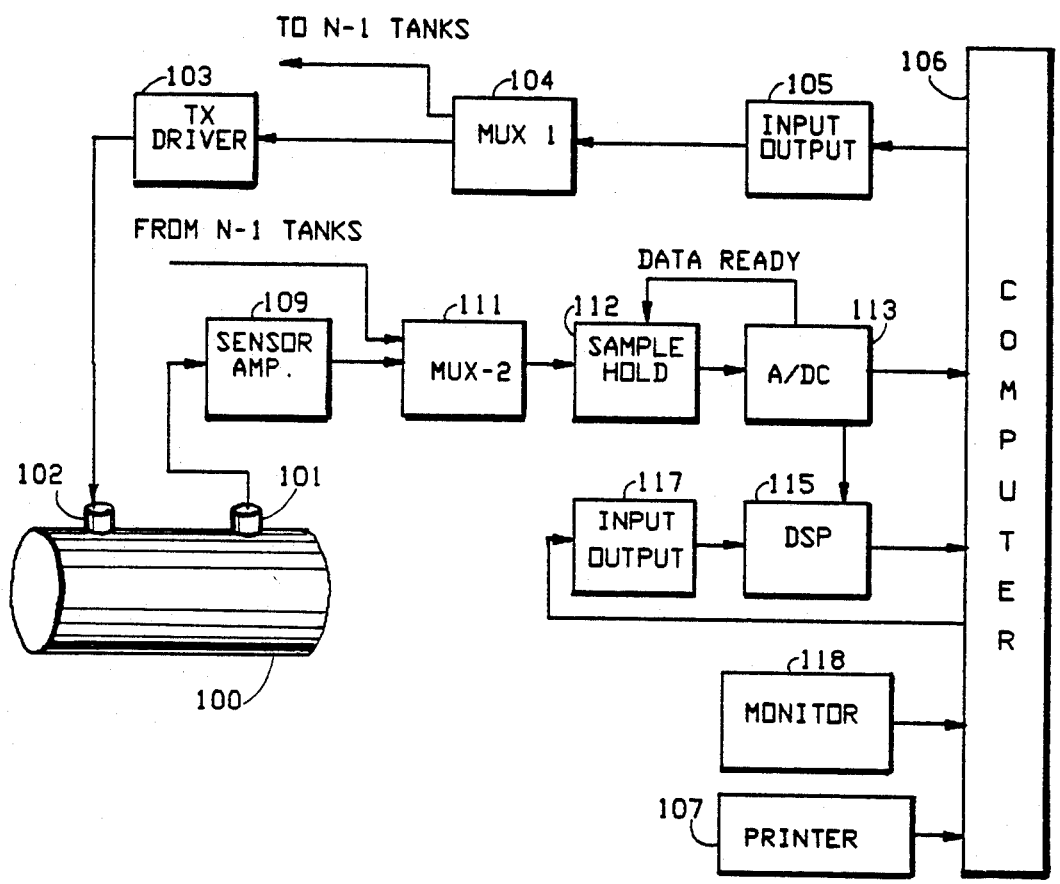

FIG. 2 illustrates in schematic form the circuitry required for measuring the liquid remaining in a large number of tanks. These tanks may report sequentially their tank content or upon interrogation annunciate their content. A desk top computer 106 is shown in FIG. 2. This computer is augmented with interface cards containing data acquisition, digital signal processing, and multiplexing components. Software functions are used to track the volume remaining in the multiple tanks and annunciate the required data. An elapsed time clock in the computer provides the time when each tank was interrogated. The software, interface hardware, and computer memory provide the closed loop control and displays required in many applications. "ZERO" and "SPAN" (or "GAIN") adjustments, corresponding to the similar adjustments described for FIG. 1, are readily incorporated in the computer memory. As the intrinsic data is nonlinear the accuracy improves exponentially as the tank is emptied. This improves the accuracy of liquid flow information acquisition at low levels of liquids. For many fuel tank applications this is a requirement and FIG. 4 illustrates the improvement in accuracy as the remaining fluid volume decreases. The number of tanks is limited only by the time required to reliably annunciate the quantity of liquid remaining in each tank. To improve the reliability in a noisy environment, digital filtering and averaging techniques are employed.

The tank 100 in FIG. 2 is shown rectangular in shape, but may be cylindrical as shown in FIG. 1. As this invention describes a volumetric gauge, the shape of the tank is irrelevant. The only structural requirements of the tank are that the material have relatively high stiffness and low dampening. Steel, aluminum, and fiberglass tanks usually qualify. A sensor, such as piezoelectric sensor "RX" 101 is required for each tank. A charge amplifier "A1" 109 interfaces between the sensor 101 and a multiplexer (MUX2) 111. A transducer driver 103 drives a transducer 102. All other components are at the computer location. A multiplexer "MUX1" 104 routes the correct driving signal to the required tank through the driver 103. An output component 105 couples the signal from the computer to the transducer driver 103. The "COMPUTER" 106 stores the acquired data in its memory, displays the data on its "MONITOR" 118, and prints the data on the "PRINTER" 107. The multiplexer "MUX2" 111 receives the dynamic data from each of the tanks upon command from the computer interface "C" 110. Sequentially, the sample and hold component 112 receives the dynamic data from its multiplexer and delivers it upon command to the analog to digital converter 113. The A/D converter 113 receives its sampling frequency from the computer timer through the (FS) interface 114. The A/D converter 113, with sufficient samples, converts the analog signal and delivers a digital block of data to the digital signal processing component "DSP" 115. The DSP 115 Performs all the mathematical computations to meet the variety of requirements. This may include correlation as a method of tone decoding, digital filtering, and linearization of data for display and recording. The DSP 115 interfaces to the computer through an input/output component "I/O" 117 and a bus interface "C" 116.

Figure 3:
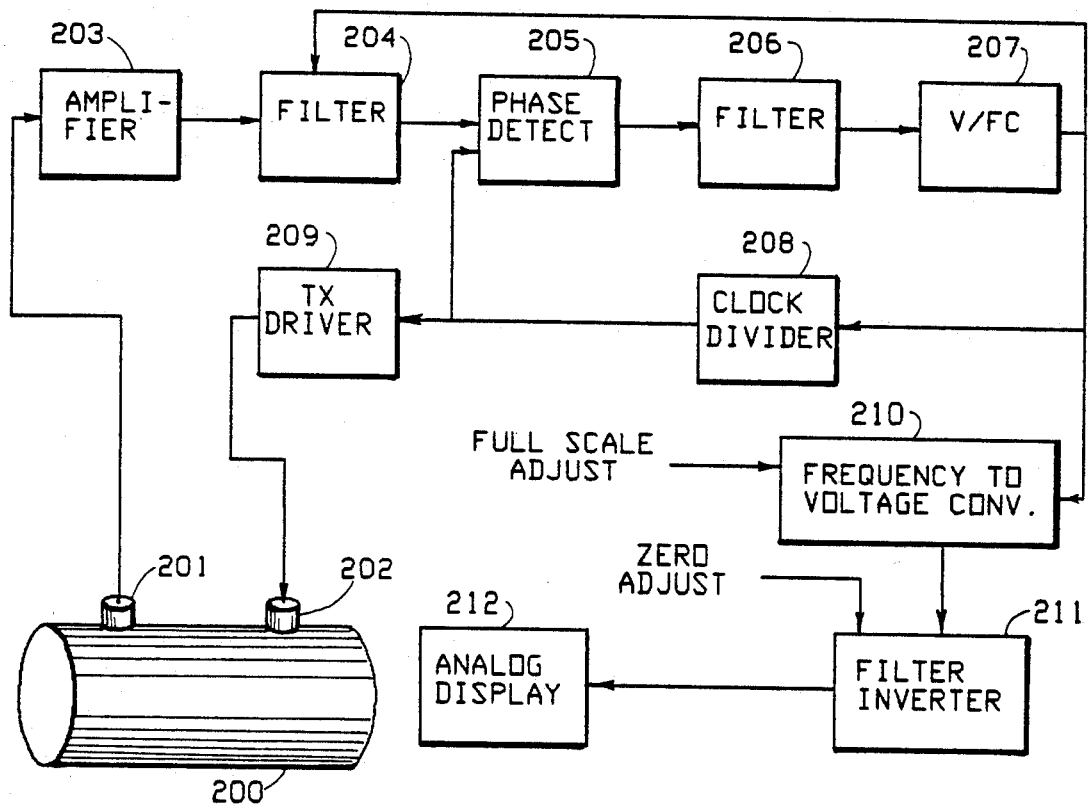

FIG. 3 describes, in schematic form, a low cost preferred embodiment of this invention. From the tank 200 to the voltage to frequency converter "VFC" 207 the circuitry and components are identical to that of FIG. 1. The output of the VFC 207 sends its resonance signal to the frequency to voltage converter 210. This component has a span adjustment, also known as a gain or full scale adjustment. The direct current voltage output of this component is connected to a filter invertor 211. This component has a zero adjustment. An optional warning signal for low fuel limits is provided for some requirements. The output of the filter invertor 211 is then connected to the input of a conventional display device, such as an analog meter 212 or digital display. Analysis of the consumer, marine and industrial market requirements have shown that the inverse exponential response of this instrument to be an advantage. The accuracy of reading increases exponentially as the fluid volume decreases. This is interesting to marine vessel operators on long voyages.

Figure 4A:
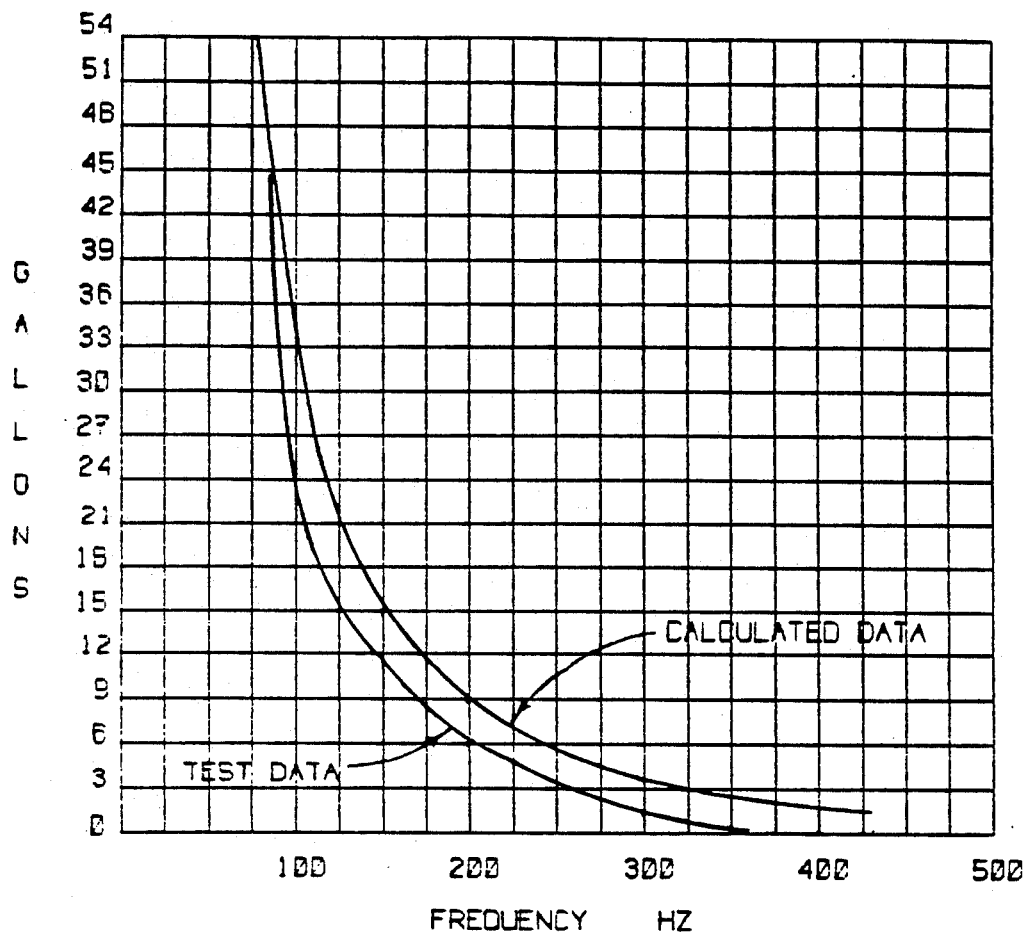
FIG. 4A is a graph illustrating the acquired test data, and calculated data for a typical fuel tank.

FIG. 4A is a graphical plot of the functional relationship between the resultant resonant frequency of the tank and the volume remaining in the tank. The frequency is considered the dependant variable. The volume of the fluid in the tank is considered the independent variable. This is justified as the fluids used in the tanks are relatively incompressible. Also, mass is considered equivalent to volume through a constant multiplier. The "ZERO" and "SPAN" adjustments compensates for all constant value considerations. From the dynamics equation of motion:

$$Fo = M\ddot{x} + C\dot{x} + kX$$

As the dampening coefficient is considered small and the stiffness is considered constant over the range of measurements:

$$Fr = \sqrt{K/M} = K'\sqrt{1/M} = K''\sqrt{1/G}$$

Of is defined as a force developed by an electrical signal applied through a transducer which drives the structure (tank) to mechanical resonance. C is defined as the dampening coefficient and is considered small. K is defined as the stiffness of the structure. Fr is defined as the resonant frequency of the tank in Hz. M in this equation is defined for diesel fuel at 57.2 pounds per cubic foot. K' in this equation is combined with other constants. K" is defined in this equation to convert mass to gallons. K" is the one parameter that is adjustable to meet the requirements of a wide variety of tanks. The "ZERO" adjustment compensates for the tare weight of the tank. The "SPAN" adjustment provides calibration of the full tank.

Figure 4B:
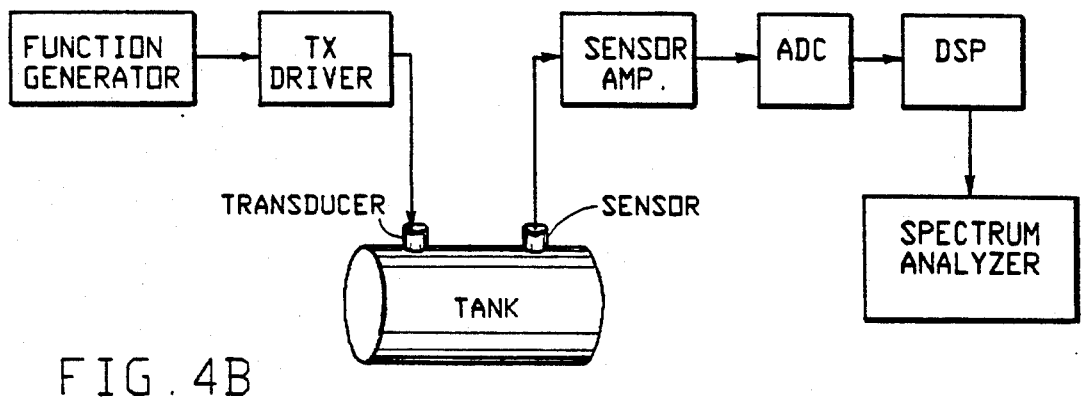
FIG. 4B is a schematic diagram of the test setup used to acquire the data illustrated in FIG. 4A.

FIG. 4B is a schematic diagram of the circuit used to acquire the data depicted in FIG. 4B. It is essentially a simplified version of the circuit shown in FIG. 2 but without the feedback from the sensor to track the tank resonance frequency, since that function is performed by the function generator.

FIG. 5 describes data acquisition circuitry similar to that of FIG. 3, but this embodiment significantly reduces the cost of the transducer and forces the burden of capability into the design of the electronic circuitry. This is provided by the electronics with little increase in cost or reduction in reliability. Differing from FIG. 3 the transducer 301 and the transducer driver 303 are no longer inside the feedback loop circuitry. The transducer driver 303 now delivers periodic narrow impulses to the transducer 301. The one-shot or impulse logic circuit 304 generates these impulses under control of a timer 305. The impulse logic circuit 304 also controls the inhibit logic 306. The inhibit logic delays the response of the charge amplifiers 307 for a predetermined time after the impulse to the tank 300. The inhibit logic also precludes the operation of the ample and hold 311 components operation for a predetermined time. The charge amplifier 307 receives a resonant periodic transient signal from the sensor 302. The band-pass filter 308 presents this filtered signal to a modified phase locked loop component 309. The output of the phase locked loop component 309 is filtered in a filter 310 and sent to a sample and hold component 311, which drives a voltage controlled oscillator 312, which in turn, closes the loop to the phase detector within the phase locked loop circuitry. The voltage controller oscillator 312 in turn drives circuitry similar to that of FIG. 3. This consists of components 313, 314, and 315.

FIG. 6 describes the embodiment of components and circuitry that will satisfy several marine instrumentation requirements. This embodiment is identical to that of FIG. 1 from the tank 400 to the voltage to frequency converter 408. The tone decoder circuitry 409 provides a novel and low cost way to annunciate the volume of fuel remaining in the tank. The display panel 410 uses a series of lights to display the volume of fuel. In FIG. 6 the circuitry is designed to annunciate an alarm when the fuel drops below 2 gallons by flashing both the 0 and 2 gallon lights. Tone decoder circuitry 411 also permits annunciation of alarms when the signature vibrations of the engine or vessel controls are outside the normal range of frequencies for various speeds. A tone decoder also provides an alarm when frequencies are present in the water that alarm fish. A charge amplifier 412 receives the alarm signals from the sensor 413.

FIG. 7 describes an embodiment of instrumentation for dual marine engines. The instrumentation includes static quantity parameters such as temperature, pressure; with the VOLUMERIC FUEL GAUGE, a dynamic measurement device. All the sensor and transducer data is controlled by the multiplexer 500. The multiplexer receives address information from on of the four momentary contact switches on the front panel. Both front panel readouts are frequency counters. Frequency decoders provide alarm annunciation.

I claim:

1. An instrument for measuring the volume of an incompressible fluid in at least one liquid container or tank, comprising:
    means for vibrating the tank at its structural resonant frequency as a function of the mass of the liquid in the tank;
    means for measuring the dynamic structural resonant frequency of the tank and liquid load;
    means for producing dynamic electrical resonance signals indicative of said structural resonant frequency and for filtering out noise frequencies;
    means for translating said dynamic electrical resonance signals into signals indicative of the liquid volume in said tank; and
    means electrically connected to said translating means for displaying the volume of said liquid in said tank in response to said volume indicating signals;
    whereby the volume of liquid remaining in the tank is displayed on said display with an accuracy that is immune to acoustic noise and an accuracy that increases as the tank becomes more empty.

2. An instrument as defined in claim 1, further comprising:
    filter means in said translating means for filtering noise components from said measurement means to provide such additional noise immunity as may be required;
    whereby, said instrument is insensitive to noise in a high vibration environment.

3. An instrument as defined in claim 1, especially adapted for measuring the volume of liquid in multiple tanks, comprising:
    multiplexer means for addressing, transmitting, and receiving dynamic data to or from said transducer and said measuring means;
    data acquisition means for translating said dynamic signals from said measurement means into digital format, under software control;
    digital signal processing means for performing mathematical operations under computer control in real time to convert said digital signals into a volumetric measure of the liquid remaining in each tank.

4. An instrument, as defined in claim 1, further comprising;
    means for converting the output of the voltage to frequency converter to a full scale adjusted direct current output signal;
    means for filtering, inverting and zero adjusting said direct current signal; and
    an analog display in said display means connected to said means for filtering for displaying the liquid volume remaining in the tank as indicated by said direct current signal;
    whereby said analog display provides a volumetric display of the volume of liquid in said tank with exponentially increased accuracy for low liquid volumes.

5. A gauge as defined in claim 1 further comprising:
    means for tracking the resonant frequency and controlling the dynamic excitation of the tank, as the liquid volume changes, by feedback control components.

6. An instrument as defined in claim 1, wherein;

said vibrating means includes a transducer adapted to excite the tank at its resonant frequency, said transducer being installed on the exterior surface of the tank out of physical contact with the liquid and the interior of said tank; and said measurement means includes a sensor, also installed on the exterior surface of said tank out of physical contact with the liquid and the interior of said tank;

whereby, said instrument is safe for the volumetric measurement of volatile or hazardous in the tank.

7. A method of measuring the liquid volume in a tank, comprising:

subjecting said tank, loaded with liquid, to periodic mechanical impulses to cause said tank to vibrate at its structural resonant frequency;

measuring the amplitude of said structural resonant vibrations;

translating said vibrations at said structural resonant frequency into signals which are in an analytic inverse exponential relationship to the quantity of liquid remaining in the tank; and displaying said liquid volume on a liquid volume indicator;

whereby said display of said liquid volume becomes increasingly accurate as said tank empties.

8. A method as defined in claim 7, further comprising:

automatically annunciating an alarm when the liquid quantity drops below a certain predetermined level.

9. A method as defined in claim 7, further comprising:

detecting with alarm instrumentation vibrations sensed by said sensor that are outside a normal signature frequency of the application or controls.

10. A method as defined in claim 7, further comprising:

simultaneously receiving data from two engines and two tanks under control of bidirectional multiplexers selecting, monitoring, and displaying two parameters simultaneously with one momentary contact switch.

11. A method as claimed in claim 7, further comprising:

subjecting said tank to periodic mechanical impulses;

adjusting the frequency of said impulses until said tank vibrates at its resonant frequency.

12. A method as defined in claim 7, further comprising:

operating a transducer driver and associated impulse generating components to vibrate said tank outside of a resonant frequency control loop;

using a signal amplifier and a sample and hold component to translate said signals, and controlling the operation of said sensor amplifier and sample and hold component using inhibit logic;

comparing transient response output of said sensor with a frequency to voltage converter during a hold period in a phase lock loop component.

13. A method as defined in claim 7, further comprising:

translating the frequency output of said frequency to voltage converter by a tone decoder into a display of liquid remaining in the tank.

14. A method as defined in claim 13, further comprising:

controlling the logic circuitry in said tone decoder circuitry with an output from a tachometer to annunciate proper alarms;

whereby vibrations which are a function of an engine rpm can be accounted for in determining when an alarm should sound.

15. A method as defined in claim 14, further comprising:

detecting vibrations, emitted by a vessel in which said tank is mounted, that alarm fish; and annunciating an alarm signal on a fish alarm annunciator when the vessel emits vibrations into the water that alarm fish.

16. An instrumented liquid holding tank for holding liquid and producing signals indicative of the liquid volume in said tank, comprising:

a tank made of stiff and rigid material, said tank having an interior wherein said liquid is contained, and an exterior surface;

a transducer and a sensor mounted on said exterior surface of said tank;

said transducer being responsive to driving signals to vibrate said tank at its structural resonant frequency; and said sensor producing signals indicative of the structural resonant frequency of said tank when vibrated by said transducer;

whereby said sensor signals may be translated into signals which are in an analytic inverse exponential relationship to the liquid volume in said tank, and displayed on a display to show the liquid volume remaining in said tank, and said display of said liquid volume becomes increasingly accurate as said tank empties.

* * * * *